(12) United States Patent
Schneider et al.

(10) Patent No.: US 9,921,183 B2
(45) Date of Patent: Mar. 20, 2018

(54) VACUUM DMS WITH HIGH EFFICIENCY ION GUIDES

(71) Applicant: DH Technologies Development Pte. Ltd., Singapore (SG)

(72) Inventors: Bradley B. Schneider, Bradford (CA); Hassan Javaheri, Richmond Hill (CA); Thomas R. Covey, Richmond Hill (CA)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 15/104,954

(22) PCT Filed: Dec. 6, 2014

(86) PCT No.: PCT/IB2014/002690
§ 371 (c)(1),
(2) Date: Jun. 15, 2016

(87) PCT Pub. No.: WO2015/101821
PCT Pub. Date: Jul. 9, 2015

(65) Prior Publication Data
US 2016/0320342 A1    Nov. 3, 2016

Related U.S. Application Data

(60) Provisional application No. 61/922,547, filed on Dec. 31, 2013, provisional application No. 61/931,793, filed on Jan. 27, 2014.

(51) Int. Cl.
*G01N 27/06*    (2006.01)
*H01J 49/04*    (2006.01)
(Continued)

(52) U.S. Cl.
CPC ........ *G01N 27/624* (2013.01); *H01J 49/0031* (2013.01); *H01J 49/063* (2013.01); *H01J 49/24* (2013.01); *H01J 49/066* (2013.01)

(58) Field of Classification Search
CPC ... G01N 27/622; G01N 27/624; H01J 49/004; H01J 49/0031; H01J 49/26; H01J 49/42;
(Continued)

(56) References Cited

U.S. PATENT DOCUMENTS 6,417,511 B1 * 7/2002 Russ, IV ............... H01J 49/063
250/292
7,138,626 B1 * 11/2006 Karpetsky ............ G01N 27/624
250/281
(Continued)

FOREIGN PATENT DOCUMENTS

EP    2455963 A2    5/2012
WO    2008055667 A2    5/2008
(Continued)

OTHER PUBLICATIONS

International Search Report and Written Opinion for PCT/IB2014/002690, dated Apr. 8, 2015.

*Primary Examiner* — David A Vanore
(74) *Attorney, Agent, or Firm* — John R. Kasha; Kelly L. Kasha; Kasha Law LLC

(57) ABSTRACT

Differential mobility spectrometry is performed under vacuum. Ions generated in a high pressure region are received from the inlet orifice of a vacuum chamber using a first ion guide located in the vacuum chamber. The first ion guide focuses the generated ions on a DMS device inlet end using a plurality of tapered electrodes. The DMS device is coaxial and adjacent to the first ion guide. The DMS device separates the focused ions using a plurality of electrodes. The inscribed diameter at the DMS device inlet end is larger than the inscribed diameter at the first ion guide exit end to
(Continued)

maximize ion transfer. The separated ions are received from the DMS device using a second ion guide coaxial and adjacent to the DMS device. The second ion guide focuses the separated ions on an exit orifice of the vacuum chamber using a plurality of tapered electrodes.

19 Claims, 4 Drawing Sheets

(51) Int. Cl.
      *H01J 49/42*       (2006.01)
      *G01N 27/62*       (2006.01)
      *H01J 49/00*       (2006.01)
      *H01J 49/24*       (2006.01)
      *H01J 49/06*       (2006.01)

(58) Field of Classification Search
    CPC ...... H01J 49/0422; H01J 49/06; H01J 49/062;
             H01J 49/063; H01J 49/065; H01J 49/066;
                        H01J 49/14; H01J 49/164
    USPC ... 250/281, 282, 288, 290, 287, 292, 396 R,
                        250/283, 286, 291, 293, 423 R
    See application file for complete search history.

(56) References Cited

U.S. PATENT DOCUMENTS

| | | | |
|---|---|---|---|
| 7,514,676 B1* | 4/2009 | Page | G01N 27/622 250/281 |
| 7,868,289 B2 | 1/2011 | Cousins et al. | |
| 8,080,787 B2* | 12/2011 | Rather | G01N 27/622 250/282 |
| 8,129,676 B2* | 3/2012 | Vestel | G01N 21/658 250/281 |
| 8,253,095 B2* | 8/2012 | Franzen | G01N 27/622 250/281 |
| 8,299,443 B1* | 10/2012 | Shvartsburg | H01J 49/0018 250/292 |
| 8,610,054 B2* | 12/2013 | Giles | G01N 27/624 250/281 |
| 9,165,753 B2* | 10/2015 | Loboda | H01J 49/164 |
| 9,177,770 B2* | 11/2015 | Osgood | G01N 27/622 |
| 2009/0173877 A1* | 7/2009 | Bateman | G01N 27/622 250/282 |
| 2011/0183431 A1* | 7/2011 | Covey | G01N 27/624 436/173 |
| 2012/0056085 A1 | 3/2012 | Roger et al. | |
| 2012/0273673 A1* | 11/2012 | Park | G01N 27/624 250/283 |
| 2016/0187296 A1* | 6/2016 | Blagojevic | G01N 27/624 250/282 |
| 2016/0320342 A1* | 11/2016 | Schneider | G01N 27/624 |

FOREIGN PATENT DOCUMENTS

| | | |
|---|---|---|
| WO | 20130636601 A1 | 5/2013 |
| WO | 2013114191 A1 | 8/2013 |

\* cited by examiner

VACUUM DMS WITH HIGH EFFICIENCY ION GUIDES

CROSS REFERENCE TO RELATED APPLICATION

This application claims the benefit of U.S. Provisional Patent Application Ser. No. 61/922,547, filed Dec. 31, 2013 and U.S. Provisional Patent Application Ser. No. 61/931,793, filed Jan. 27, 2014, the content of which is incorporated by reference herein in its entirety.

INTRODUCTION

Differential mobility spectrometry (DMS) devices are typically operated at atmospheric pressure. Placing a DMS device into the vacuum system of a mass spectrometer may provide benefits, such as the possibility to permanently leave the device mounted with on/off control electrically actuated. However, it is important to ensure that the DMS device does not degrade ion transmission through the entrance optics of the mass spectrometer.

SUMMARY

A system is disclosed for performing differential mobility spectrometry (DMS) under vacuum. The system includes a vacuum chamber, a first ion guide, a DMS device, and a second ion guide. The vacuum chamber includes an inlet orifice for receiving ions from a high pressure region into the vacuum chamber. The vacuum chamber further includes an exit orifice for sending ions from the vacuum chamber. The first ion guide is located in the vacuum chamber. The first ion guide receives ions from the inlet orifice of the vacuum chamber. The first ion guide has a first inlet end and a first exit end. The first ion guide has a plurality of first electrodes arranged around a central axis defining a first ion channel. Each of the plurality of first electrodes is tapered to provide a larger inscribed diameter at the first inlet end than at the first exit end in order to focus ions in the first ion channel.

The DMS device is located in the vacuum chamber coaxially and adjacent to the first ion guide. The DMS device receives ions from the first exit end of the first ion guide. The DMS device has a DMS inlet end and a DMS exit end. The inscribed diameter at the DMS inlet end is larger than the inscribed diameter at the first exit end of the first ion guide to minimize the loss of ions from the first ion guide to the DMS device. The DMS device has a plurality of DMS electrodes arranged around a central axis defining a DMS ion channel with a constant gap in order to separate ions within the DMS ion channel.

The second ion guide is located in the vacuum chamber coaxially and adjacent to the DMS device. The second ion guide receives ions from the DMS exit end and focuses the ions on the exit orifice of the vacuum chamber. The second ion guide has a second inlet end and a second exit end. The inscribed diameter at the second inlet end is larger than the inscribed diameter at the DMS exit end to minimize the loss of ions from the DMS device to the second ion guide. The second ion guide has a plurality of second electrodes arranged around a central axis defining a second ion channel. Each of the plurality of second electrodes is tapered to provide a larger inscribed diameter at the second inlet end than at the second exit end in order to focus ions in the second ion channel.

In a preferred embodiment, the system further includes a housing that encloses the DMS device. The housing is used to optimize the pressure in the DMS device. For example, the housing allows the DMS device to operate at a pressure greater than both the first ion guide and the second ion guide. The housing includes in inlet aperture for passing ions from the first ion guide to the DMS device. The housing includes an exit aperture for passing ions from the DMS device to the second ion guide. The housing also includes a gas inlet. The gas inlet receives gas to increase pressure in the housing above a pressure of the vacuum chamber, for example.

A method is disclosed for performing DMS under vacuum. Generated ions are received from a high pressure region using a vacuum chamber. The vacuum chamber includes an inlet orifice for receiving the generated ions from the high pressure region into the vacuum chamber. The vacuum chamber further includes an exit orifice for sending ions from the vacuum chamber. The generated ions are received from the inlet orifice of the vacuum chamber using a first ion guide located in the vacuum chamber that focuses the generated ions. The first ion guide has a first inlet end and a first exit end. The first ion guide has a plurality of first electrodes arranged around a central axis defining a first ion channel. Each of the plurality of first electrodes is tapered to provide a larger inscribed diameter at the first inlet end than at the first exit end in order to focus ions in the first ion channel.

The focused ions are received from the first ion guide using a DMS device. The DMS device is located in the vacuum chamber coaxially and adjacent to the first ion guide that separates the focused ions. The DMS device has a DMS inlet end and a DMS exit end. The inscribed diameter at the DMS inlet end is larger than the inscribed diameter at the first exit end of the first ion guide to minimize the loss of ions from the first ion guide to the DMS device. The DMS device has a plurality of DMS electrodes arranged around a central axis defining a DMS ion channel with a constant gap in order to separate ions within the DMS ion channel.

The separated ions are received from the DMS device using a second ion guide. The second ion guide is located in the vacuum chamber coaxially and adjacent to the DMS device. The second ion guide focuses the separated ions on the exit orifice of the vacuum chamber. The second ion guide has a second inlet end and a second exit end. The inscribed diameter at the second inlet end is larger than the inscribed diameter at the DMS exit end to minimize the loss of ions from the DMS device to the second ion guide. The second ion guide has a plurality of second electrodes arranged around a central axis defining a second ion channel. Each of the plurality of second electrodes is tapered to provide a larger inscribed diameter at the second inlet end than at the second exit end in order to focus ions in the second ion channel.

These and other features of the applicant's teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

Figure 1:
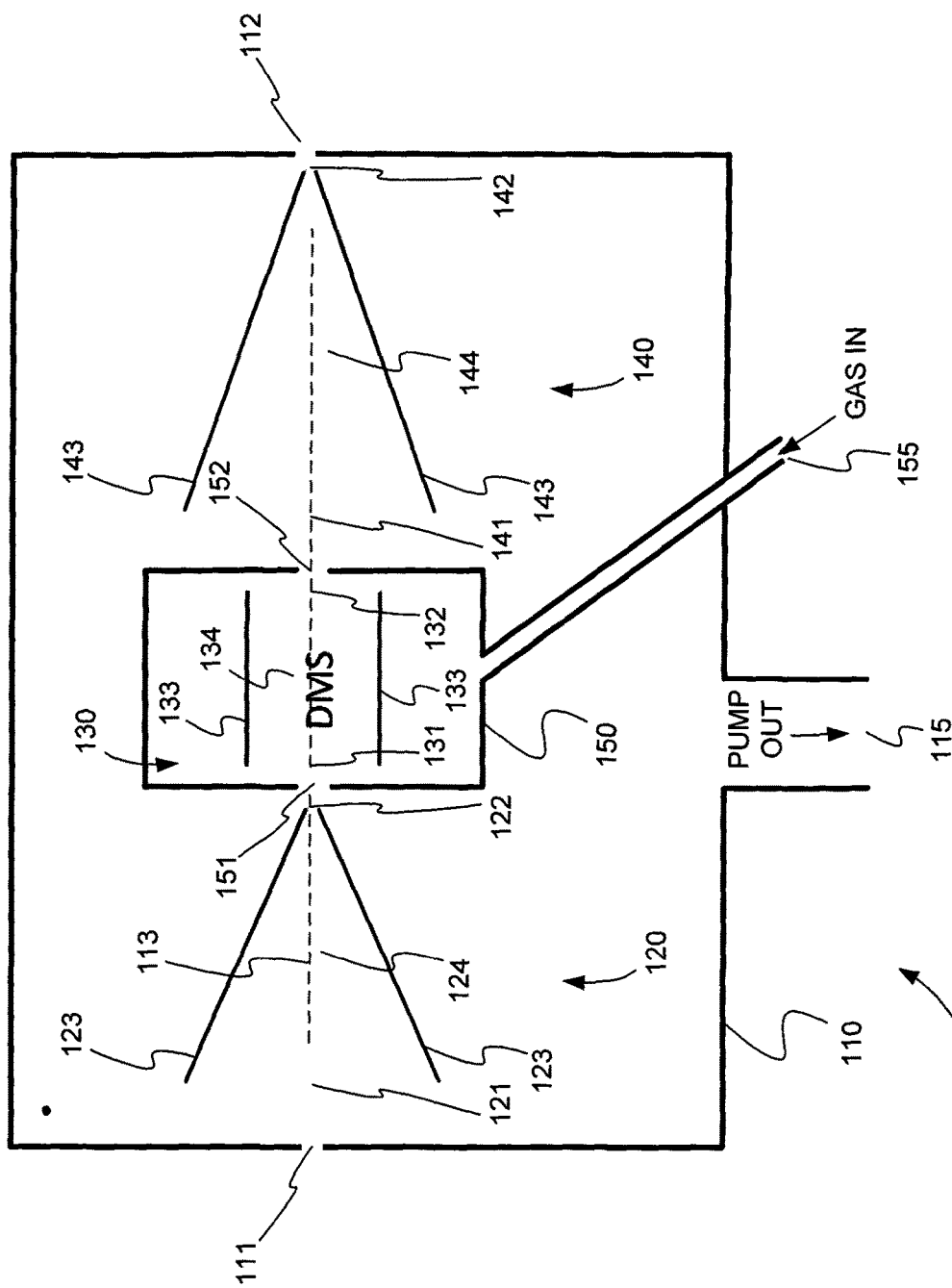
FIG. 1 is a schematic diagram of a system for performing differential mobility spectrometry (DMS) under vacuum, in accordance with various embodiments.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

As described above, placing a differential mobility spectrometry (DMS) device into the vacuum system of a mass spectrometer may allow the device to remain permanently mounted to the spectrometer. However, no system has yet been developed that provides an efficient means for capturing ions from a free jet expansion.

In various embodiments, a segmented radio frequency (RF) multipole configuration within the vacuum system of a mass spectrometer provides an efficient means for capturing ions from a free jet expansion for DMS. Specifically, ion guides (as opposed to lenses) are used to provide high efficiency ion transmission. The segments include a first RF multipole ion guide, a multipole DMS device at the exit of the first RF ion guide, and a second RF multipole ion guide at the exit of the DMS device. The first RF ion guide includes an inscribed diameter at the inlet sufficient to accept at least 50% of the diameter of the barrel shock surrounding a free jet gas expansion into the vacuum chamber, for example. The first RF ion guide is tapered such that the captured ions are focused prior to the outlet. The exit dimension of the first RF ion guide is smaller than the inlet dimensions of the DMS device in order to minimize the loss of ions upon transfer to the DMS device. Ions can then be separated within the DMS device.

The second RF ion guide is also tapered. The second RF ion guide has an inscribed diameter at the inlet greater than the exit dimension of the DMS device. The taper of the second RF ion guide focuses mobility filtered ions prior to an aperture that separates differentially pumped vacuum regions. The DMS device can be enclosed in a housing such that the gas flow from the outlet of the differentially pumped vacuum chamber draws laminar flow streamlines through the DMS device. Additionally, the lengths of the first RF ion guide and the second RF ion guide can be optimized to ensure sufficient focusing properties and elimination of detrimental beaming/shock waves. Focusing potentials can also be applied to the DMS device to improve transmission.

System for DMS under Vacuum

FIG. 1 is a schematic diagram of a system 100 for performing DMS under vacuum, in accordance with various embodiments. System 100 includes vacuum chamber 110, first ion guide 120, DMS device 130, and second ion guide 140. First ion guide 120 and second ion guide 140 are, for example, RF ion guides, and are each supplied by a power supply providing RF voltage.

Vacuum chamber 110 includes inlet orifice 111 for receiving ions from a high pressure region into vacuum chamber 110 and exit orifice 112 for sending ions from vacuum chamber 110. An ion source (not shown), for example, generates ions from a sample in the high pressure region (not shown). Vacuum chamber 110 also includes pump port 115.

A roughing pump can be attached to pump port 115 to provide control of the pressure in vacuum chamber 110, for example.

First ion guide 120 is located in vacuum chamber 110. First ion guide 120 receives ions from inlet orifice 111. First ion guide 120 has first inlet end 121 and first exit end 122. First ion guide 120 has a plurality of first electrodes 123 arranged around central axis 113 defining first ion channel 124. Each of the plurality of first electrodes 123 is tapered to provide a larger inscribed diameter at first inlet end 121 than at first exit end 122 in order to focus ions in first ion channel 124.

DMS device 130 is located in vacuum chamber 110 coaxially and adjacent to first ion guide 120. DMS device 130 receives ions from first exit end 122 of first ion guide 120. DMS device 130 has DMS inlet end 13 land DMS exit end 132. The inscribed diameter at DMS inlet end 131 is larger than the inscribed diameter at first exit end 122 of first ion guide 120 in order to minimize the loss of ions from first ion guide 120 to DMS device 130. DMS device 130 has a plurality of DMS electrodes 133 arranged around central axis 113. The plurality of DMS electrodes 133 define DMS ion channel 134 that has a constant gap in order to separate ions within DMS ion channel 134.

Second ion guide 140 is located in vacuum chamber 110 coaxially and adjacent to first DMS device 130. Second ion guide 140 receives ions from DMS exit end 132 of DMS device 130. Second ion guide 140 focuses the ions on exit orifice 112 of vacuum chamber 110. Second ion guide 140 has second inlet end 141 and second exit end 142. The inscribed diameter at second inlet end 141 is larger than the inscribed diameter at DMS exit end 132 in order to minimize the loss of ions from DMS device 130 to second ion guide 140. Second ion guide 140 has a plurality of second electrodes 143 arranged around central axis 113 defining second ion channel 144. Each of the plurality of second electrodes 143 is tapered to provide a larger inscribed diameter at second inlet end 141 than at second exit end 142 in order to focus ions in second ion channel 144.

In various embodiments, system 100 further includes housing 150 that encloses DMS device 130. Housing 150 is used to allow DMS device 130 to operate at a pressure greater than both first ion guide 120 and second ion guide 140. RF ion guides perform better in intermediate pressure regimes, and DMS devices perform better at still higher pressures. For example, first ion guide 120 and second ion guide 140 are operated at pressures less than 20 Torr, and DMS device 130 is operated at pressures higher than 20 Torr. In various embodiments, DMS device 130 is operated at a pressure 10 times higher than first ion guide 120 and second ion guide 140. In other embodiments, the DMS pressure may be optimized at the same pressure as the vacuum chamber 110, or any pressure over a range extending from the same as chamber 110 to atmospheric pressure, or greater. It should be noted that higher pressures in the DMS cell would require a larger vacuum pump to maintain a given pressure in chamber 110 due to outflow of gas from apertures 151 and 152.

Housing 150 includes inlet aperture 151 for passing ions from first ion guide 120 to DMS device 130. Housing 150 includes exit aperture 152 for passing ions from DMS device 130 to second ion guide 140. Housing 150 also includes gas inlet 155. Gas inlet 155 receives gas to increase pressure in housing 150 above a pressure of vacuum chamber 110, for example.

It is important to note that DMS device 130 is operated at a pressure greater than both first ion guide 120 and second ion guide 140 not by evacuating vacuum chamber 110 and housing 150 to different pressure levels. Instead, DMS device 130 is operated at a pressure greater than both first ion guide 120 and second ion guide 140 by introducing gas into housing 150 through gas inlet 155 to increase pressure in housing 150 above a pressure of vacuum chamber 110.

In various embodiments, a planar surface of each of the plurality of tapered first electrodes 123 faces the interior of first ion guide 120 and is gradually narrowed and tilted inward to provide a smaller inscribed diameter at first exit end 122 than at first inlet end 121 of first ion guide 120. Likewise, a planar surface of each of the plurality of tapered second electrodes 143 faces the interior of second ion guide 140 and is gradually narrowed and tilted inward to provide a smaller inscribed diameter at second exit end 142 than at second inlet end 141 of second ion guide 140.

In various embodiments, first ion guide 120, DMS device 130, or second ion guide 140 can be a multipole device. First ion guide 120, DMS device 130, and second ion guide 140 can include any multiple of two electrodes. For example, first ion guide 120, DMS device 130, or second ion guide 140 can include four electrodes, six electrodes, eight electrodes, ten electrodes, twelve electrodes, fourteen electrodes, sixteen electrodes, etc.

In various embodiments, an asymmetric separation field and a DC compensation field are applied to the DMS device when filtering is desired, and applying a focusing RF potential when the DMS is not filtering. The asymmetric separation field, the DC compensation field, and the focusing RF potential are applied using any means capable of switching voltages or electric fields under programmatic control. This means can include, but is not limited to, a processor, a controller, an application specific digital circuit, or an application specific analog circuit.

Figure 2:
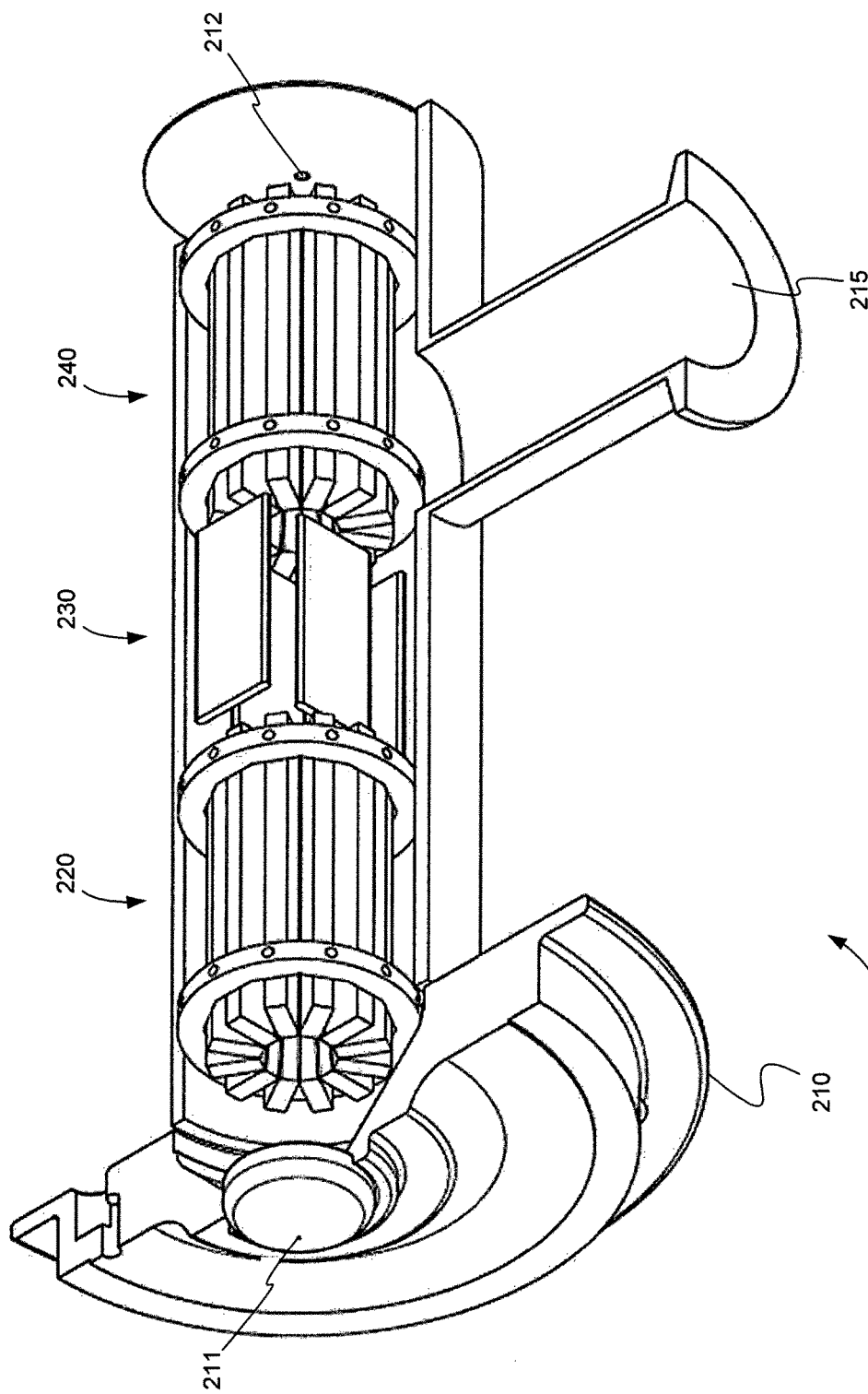
FIG. 2 is a front view of a system for performing DMS under vacuum that includes a four electrode DMS device, in accordance with various embodiments.

FIG. 2 is a front view of a system 200 for performing DMS under vacuum that includes a four electrode DMS device 240, in accordance with various embodiments. Vacuum chamber 210 includes inlet orifice 211, an exit orifice 212, and pump port 215. The location of pump port 215 can be moved to the back of vacuum chamber 210 to provide gas flow towards the back of vacuum chamber 210. Vacuum chamber 210 can be any type of sleeve or enclosure, for example.

First ion guide 220, DMS device 230, and second ion guide 240 are part of a segmented ion guide located in vacuum chamber 210. First ion guide 220 and second ion guide 240 are tapered dodecapole devices. DMS device 230 includes four flat plates as electrodes. The DMS separation waveform may be applied between 2 of the opposite-facing electrodes. Further DC or RF potentials may be applied to the other pair of electrodes. When DMS separation is not desired, a symmetrical RF focusing potential may be applied to the 4 electrodes to ensure high transmission.

Figure 3:
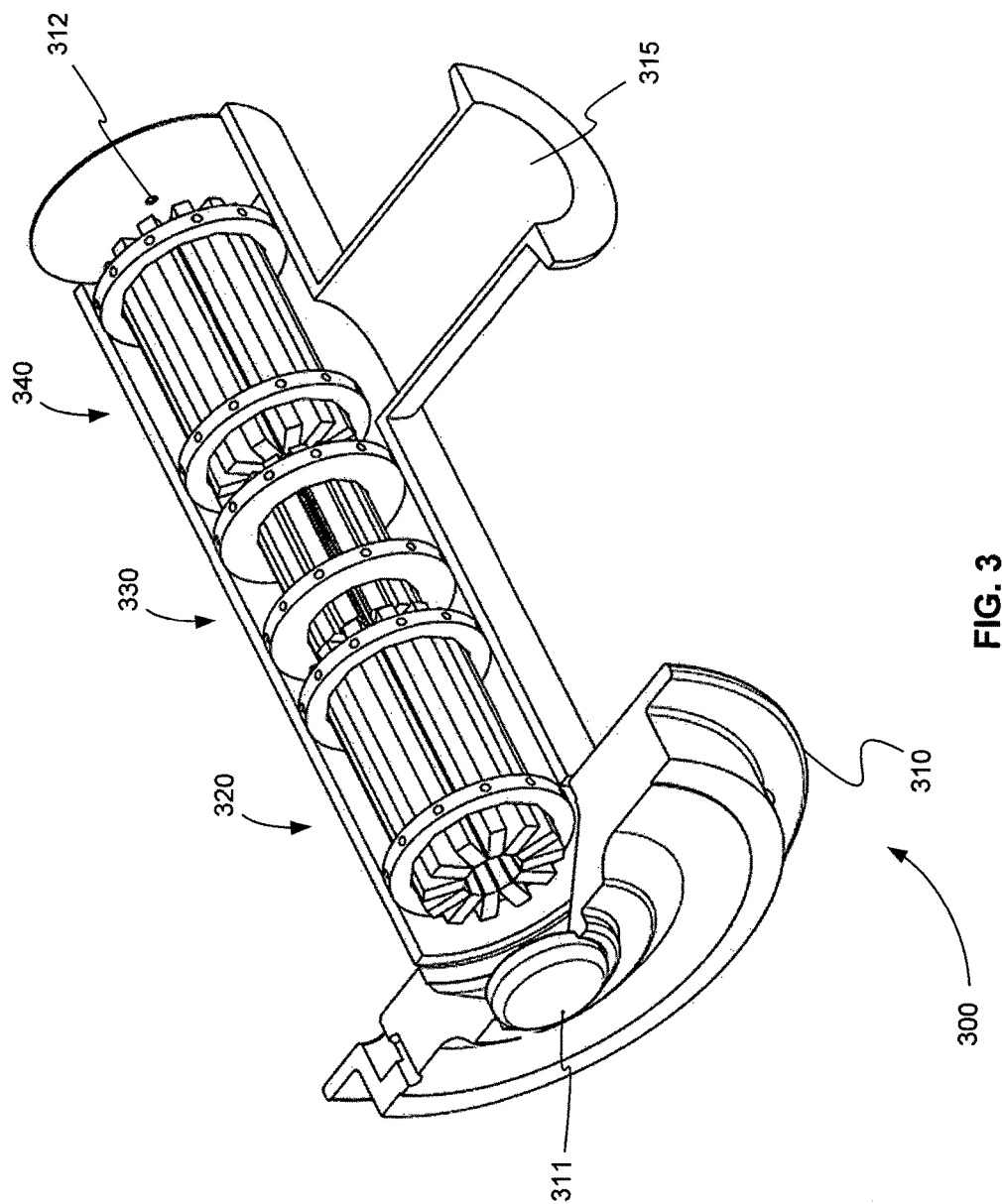
FIG. 3 is a front view of a system for performing DMS under vacuum that includes a twelve electrode DMS device, in accordance with various embodiments.

FIG. 3 is a front view of a system 300 for performing DMS under vacuum that includes a twelve electrode DMS device 340, in accordance with various embodiments. Vacuum chamber 310 includes inlet orifice 311, exit orifice 312, and pump port 315. First ion guide 320, DMS device 330, and second ion guide 340 are part of a segmented ion guide located in vacuum chamber 310. First ion guide 320 and second ion guide 340 are tapered dodecapole devices. DMS device 330 is a non-tapered dodecapole device. DMS waveforms may be applied to the dodecapole device when filtering is desired, and a focusing RF potential may be applied when filtering is not desired.

Method for DMS under Vacuum

Figure 4:
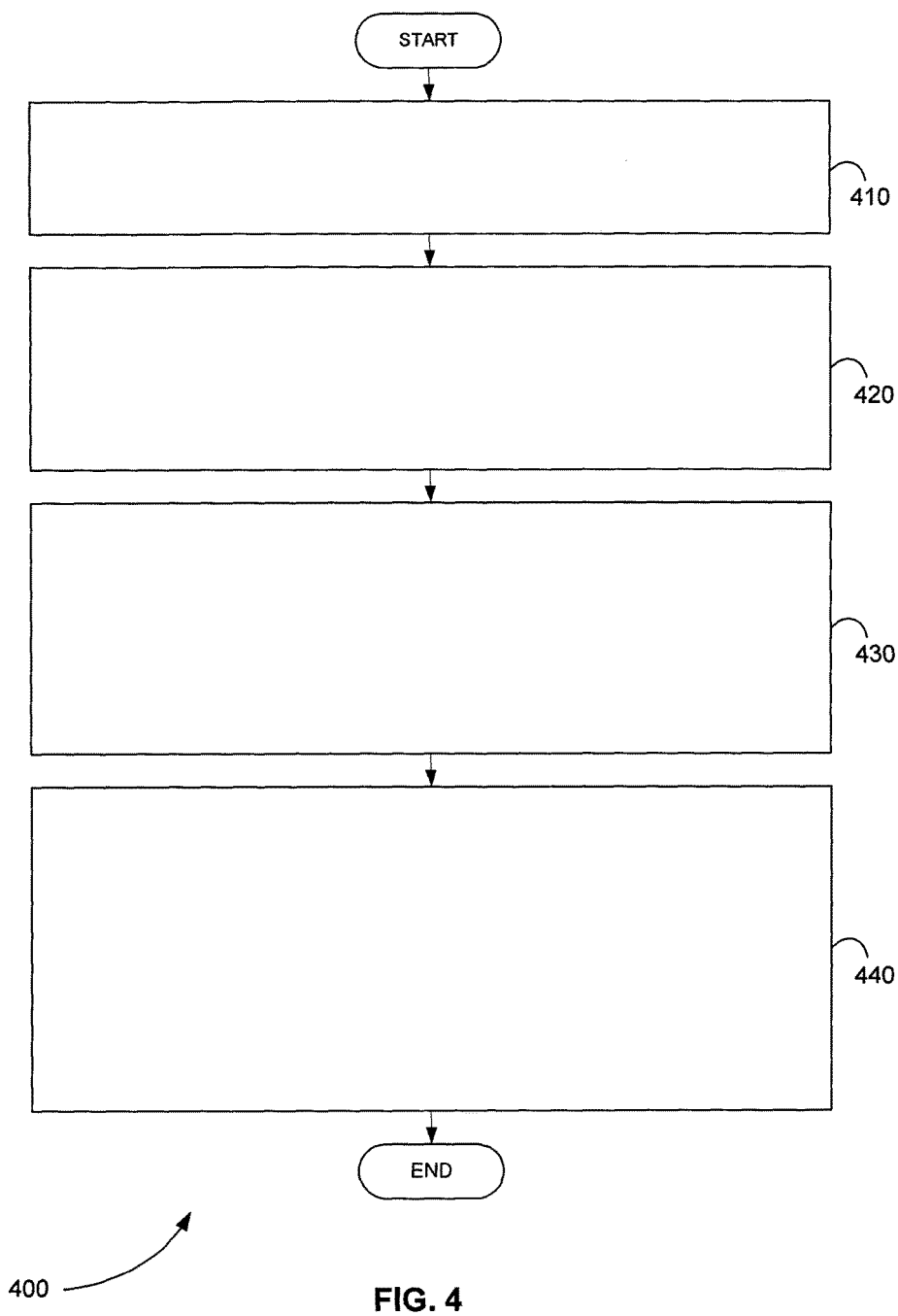
FIG. 4 is a flowchart showing a method for performing DMS under vacuum, in accordance with various embodiments.

FIG. 4 is a flowchart showing a method 400 for performing DMS under vacuum, in accordance with various embodiments.

In step 410 of method 400, generated ions are received from a high pressure region using a vacuum chamber. The vacuum chamber includes an inlet orifice for receiving the generated ions from the high pressure region into the vacuum chamber and an exit orifice for sending ions from the vacuum chamber.

In step 420, the generated ions are received from the inlet orifice using a first ion guide located in the vacuum chamber. The first ion guide focuses the generated ions. The first ion guide has a first inlet end and a first exit end. The first ion guide has a plurality of first electrodes arranged around a central axis defining a first ion channel. Each of the plurality of first electrodes are tapered to provide a larger inscribed diameter at the first inlet end than at the first exit end in order to focus ions in the first ion channel.

In step 430, the focused ions are received from the first ion guide using a DMS device located in the vacuum chamber coaxially and adjacent to the first ion guide. The DMS device separates the focused ions. The DMS device has a DMS inlet end and a DMS exit end. The inscribed diameter at the DMS inlet end is larger than the inscribed diameter at the first exit end of the first ion guide to minimize the loss of ions from the first ion guide to the DMS device. The DMS device has a plurality of DMS electrodes arranged around a central axis defining a DMS ion channel with a constant gap in order to separate ions within the DMS ion channel.

In step 440, the separated ions are received from the DMS device using a second ion guide located in the vacuum chamber coaxially and adjacent to the DMS device. The second ion guide focuses the separated ions on the exit orifice. The second ion guide has a second inlet end and a second exit end. The inscribed diameter at the second inlet end is larger than the inscribed diameter at the DMS exit end to minimize the loss of ions from the DMS device to the second ion guide. The second ion guide has a plurality of second electrodes arranged around a central axis defining a second ion channel. Each of the plurality of second electrodes is tapered to provide a larger inscribed diameter at the second inlet end than at the second exit end in order to focus ions in the second ion channel.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for performing differential mobility spectrometry (DMS) under vacuum, comprising:
   a vacuum chamber including an inlet orifice for receiving ions from a high pressure region into the vacuum chamber and an exit orifice for sending ions from the vacuum chamber;
   a first ion guide located in the vacuum chamber that receives ions from the inlet orifice, the first ion guide having a first inlet end and a first exit end, the first ion guide having a plurality of first electrodes arranged around a central axis defining a first ion channel, and each of the plurality of first electrodes being tapered to provide a larger inscribed diameter at the first inlet end than at the first exit end in order to focus ions in the first ion channel;

a DMS device located in the vacuum chamber coaxially and adjacent to the first ion guide that receives ions from the first exit end, the DMS device having a DMS inlet end and a DMS exit end, the inscribed diameter at the DMS inlet end being larger than the inscribed diameter at the first exit end to minimize the loss of ions from the first ion guide to the DMS device, the DMS device having a plurality of DMS electrodes arranged around a central axis defining a DMS ion channel with a constant gap in order to separate ions within the DMS ion channel; and a second ion guide located in the vacuum chamber coaxially and adjacent to the DMS device that receives ions from the DMS exit end and focuses the ions on the exit orifice, the second ion guide having a second inlet end and a second exit end, the inscribed diameter at the second inlet end being larger than the inscribed diameter at the DMS exit end to minimize the loss of ions from the DMS device to the second ion guide, the second ion guide having a plurality of second electrodes arranged around a central axis defining a second ion channel, and each of the plurality of second electrodes being tapered to provide a larger inscribed diameter at the second inlet end than at the second exit end in order to focus ions in the second ion channel, wherein a planar surface of each of the plurality of tapered first electrodes faces the interior of the first ion guide and is gradually narrowed and tilted inward to provide a smaller inscribed diameter at the first exit end than at the first inlet end, and wherein a planar surface of each of the plurality of tapered second electrodes faces the interior of the second ion guide and is gradually narrowed and tilted inward to provide a smaller inscribed diameter at the second exit end than at the second inlet end.

2. The system of claim 1, further comprising a housing enclosing the DMS device including an inlet aperture for passing ions from the first ion guide to the DMS device, an exit aperture for passing ions from the DMS device to the second ion guide, and a gas inlet.

3. The system of claim 2, wherein the gas inlet receives gas to increase pressure in the housing above a pressure of the vacuum chamber system.

4. The system of claim 1, wherein the first ion guide comprises a first multipole.

5. The system of claim 4, wherein the first multipole is selected from one of any multiple of two electrodes.

6. The system of claim 1, wherein the second ion guide comprises a second multipole.

7. The system of claim 6, wherein the second multipole is selected from one of any multiple of two electrodes.

8. The system of claim 1, wherein the DMS device comprises a DMS multipole.

9. The system of claim 8, wherein the DMS multipole is selected from one of any multiple of two electrodes.

10. The system of claim 1 including means to provide an asymmetric separation field and a DC compensation field to the DMS device when filtering is desired, and a focusing RF potential when filtering is not desired.

11. A method for performing differential mobility spectrometry (DMS) under vacuum, comprising:

receiving generated ions from a high pressure region using a vacuum chamber that includes an inlet orifice for receiving the generated ions from the high pressure region into the vacuum chamber and an exit orifice for sending ions from the vacuum chamber;

receiving the generated ions from the inlet orifice using a first ion guide located in the vacuum chamber that focuses the generated ions, the first ion guide having a first inlet end and a first exit end, the first ion guide having a plurality of first electrodes arranged around a central axis defining a first ion channel, and each of the plurality of first electrodes being tapered to provide a larger inscribed diameter at the first inlet end than at the first exit end in order to focus ions in the first ion channel;

receiving the focused ions from the first ion guide using a DMS device located in the vacuum chamber coaxially and adjacent to the first ion guide that separates the focused ions, the DMS device having a DMS inlet end and a DMS exit end, the inscribed diameter at the DMS inlet end being larger than the inscribed diameter at the first exit end to minimize the loss of ions from the first ion guide to the DMS device, the DMS device having a plurality of DMS electrodes arranged around a central axis defining a DMS ion channel with a constant gap in order to separate ions within the DMS ion channel; and receiving the separated ions from the DMS device using a second ion guide located in the vacuum chamber coaxially and adjacent to the DMS device that focuses the separated ions on the exit orifice, the second ion guide having a second inlet end and a second exit end, the inscribed diameter at the second inlet end being larger than the inscribed diameter at the DMS exit end to minimize the loss of ions from the DMS device to the second ion guide, the second ion guide having a plurality of second electrodes arranged around a central axis defining a second ion channel, and each of the plurality of second electrodes being tapered to provide a larger inscribed diameter at the second inlet end than at the second exit end in order to focus ions in the second ion channel, wherein a planar surface of each of the plurality of tapered first electrodes faces the interior of the first ion guide and is gradually narrowed and tilted inward to provide a smaller inscribed diameter at the first exit end than at the first inlet end, and wherein a planar surface of each of the plurality of tapered second electrodes faces the interior of the second ion guide and is gradually narrowed and tilted inward to provide a smaller inscribed diameter at the second exit end than at the second inlet end.

12. The method of claim 11, wherein receiving the focused ions from the first ion guide comprises receiving the focused ions through an inlet aperture of a housing enclosing the DMS device, the housing including the inlet aperture for passing ions from the first ion guide to the DMS device, an exit aperture for passing ions from the DMS device to the second ion guide, and a gas inlet.

13. The method of claim 12, further comprising:

receiving gas through the gas inlet to increase pressure in the housing above a pressure of the vacuum chamber system.

14. The method of claim 11, further comprising:
applying an asymmetric separation field and a DC compensation field to the DMS device when filtering is desired, and applying a focusing RF potential when filtering is not desired.

15. The method of claim 11, wherein the first ion guide comprises a first multipole.

16. The method of claim 15, wherein the first muitipole is selected from one of any multiple of two electrodes.

17. The method of claim 11, wherein the second ion guide comprises a second multipole.

18. The method of claim 17, wherein the second multipole is selected from one of any multiple of two electrodes.

19. The method of claim 11, wherein the DMS device comprises a DMS multipole.

* * * * *